United States Patent [19]

Rashidi

[11] Patent Number: 5,552,713
[45] Date of Patent: Sep. 3, 1996

[54] METHOD AND DEVICE FOR TESTING ELECTROPHYSIOLOGY CATHETER

[75] Inventor: Majid Rashidi, Beachwood, Ohio

[73] Assignee: Cardiac Assist Devices, Inc., Cleveland, Ohio

[21] Appl. No.: 290,148

[22] Filed: Aug. 15, 1994

[51] Int. Cl.$^6$ .................................................. G01R 31/12
[52] U.S. Cl. ........................... 324/555; 324/527; 324/556
[58] Field of Search ................................... 324/522, 527, 324/537, 555, 556, 542; 604/280, 281, 282, 284

[56] References Cited

U.S. PATENT DOCUMENTS

| 4,857,857 | 8/1989 | Valenti et al. | 324/555 |
| 5,396,181 | 3/1995 | O'Brien et al. | 324/556 |

*Primary Examiner*—Kenneth A. Wieder
*Assistant Examiner*—Diep Do
*Attorney, Agent, or Firm*—Roger A. Johnston

[57] ABSTRACT

A continuity/leakage tester for cardiac catheter probes of the type having plural spaced surface electrodes thereon. The apparatus includes a block having an open ended blind bores provided therein sized for receiving catheters of different diameters. A port is provided in the bore or bores adjacent the opened end and a spring loaded electrical contact provided therein which is grounded. Four plural bores are provided in the block, a common electrical conductor bar extends transversely across the ports which are formed at a common longitudinal station on each of the bores. The catheter is inserted in the bore and as each surface electrode contacts the spring biased electrode in the bore, a continuity test may be performed by an ohm meter connected to the probe lead for that particular surface electrode. As each subsequent surface electrode on the probe enters the bore, its corresponding electrical lead may be switched to the ohm meter for continuity testing of that electrode. Leakage test may be performed between each pair of spaced surface electrodes on the probe by applying a leak test voltage across any two conductors via the catheter leads. If any electrical leakage is present between the selected conductors, a leak current is detected by a leakage detector. The block may be mounted conveniently on a cabinet containing the electrical circuitry for the continuity and leakage testing; and, selector knobs may be provided on the cabinet for the various test functions. The apparatus and method of the present invention enable the medical practitioner to quickly and easily test a cardiac catheter probe in the operating room prior to insertion of the probe in the incision made for entering the probe in the patients vein and inserting the probe into the patients heart.

8 Claims, 4 Drawing Sheets

– LEAKAGE/CONTINUITY SOCKET (LCS), A SIDE VIEW SECTION
(AN EPS CATHETER PARTIALLY INSERTED INTO THE TEST BORE)

SCHEMATIC VIEW OF A CATHETER APPLICATION
FOR AN ELECTROPHYSIOLOGY STUDY

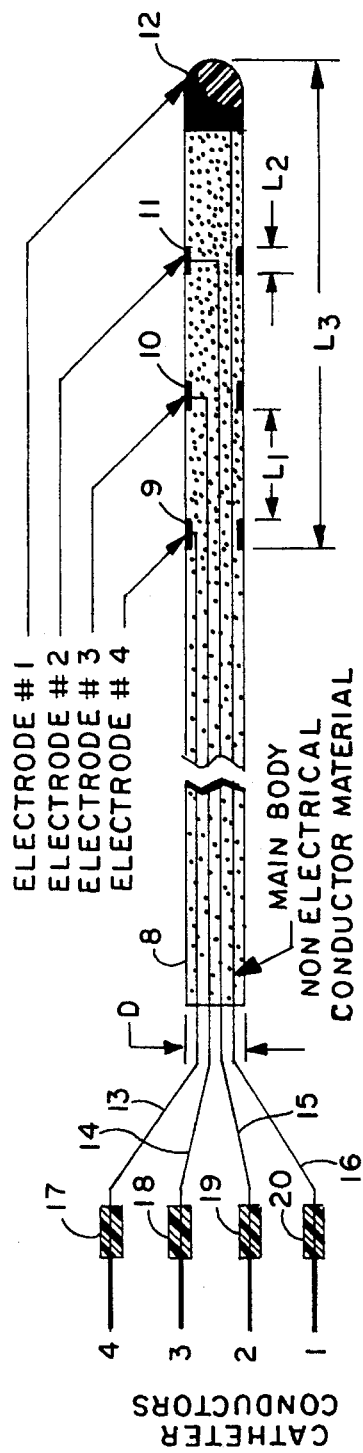
FIG. 2 – TYPICAL QUADRA-POLAR ELECTROPHYSIOLOGY CATHETER
D = CATHETER DIAMETER
$L_1$ = SPACING BETWEEN ELECTRODES
$L_2$ = ELECTRODE WIDTH
$L_3$ = SPACING BETWEEN THE FIRST AND LAST ELECTRODES
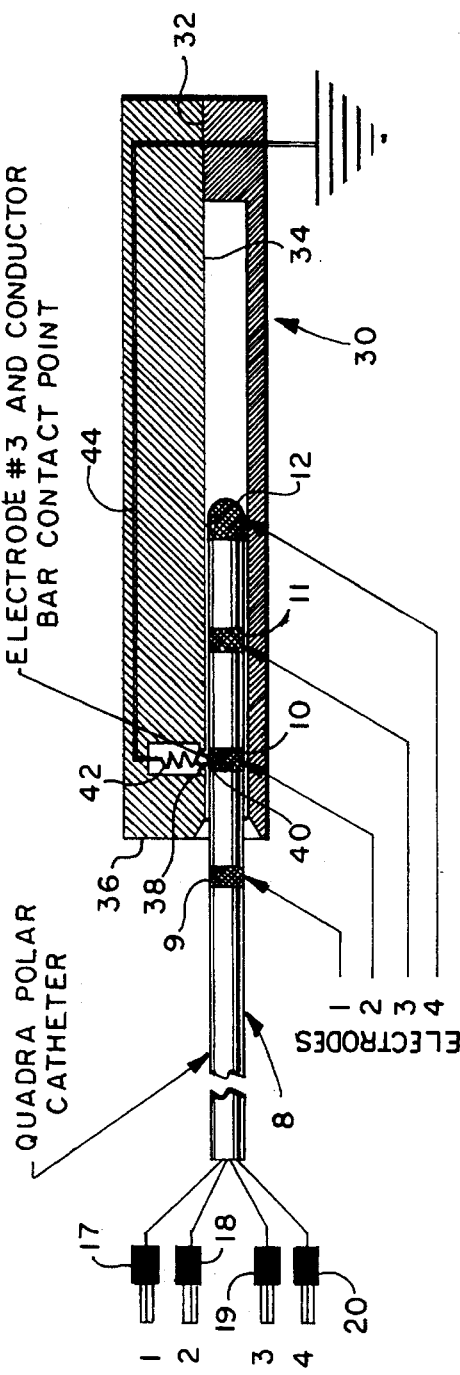
FIG. 3 – LEAKAGE/CONTINUITY SOCKET (LCS), A SIDE VIEW SECTION
(AN EPS CATHETER PARTIALLY INSERTED INTO THE TEST BORE)

TYPICAL ELECTRODE-TO-CONDUCTOR
CONTINUITY TEST (ELECTRODE #3 AND CONDUCTOR #3)

TYPICAL CONDUCTOR-TO-CONDUCTOR
LEAKAGE TEST (CONDUCTOR #1 AND CONDUCTOR #4)

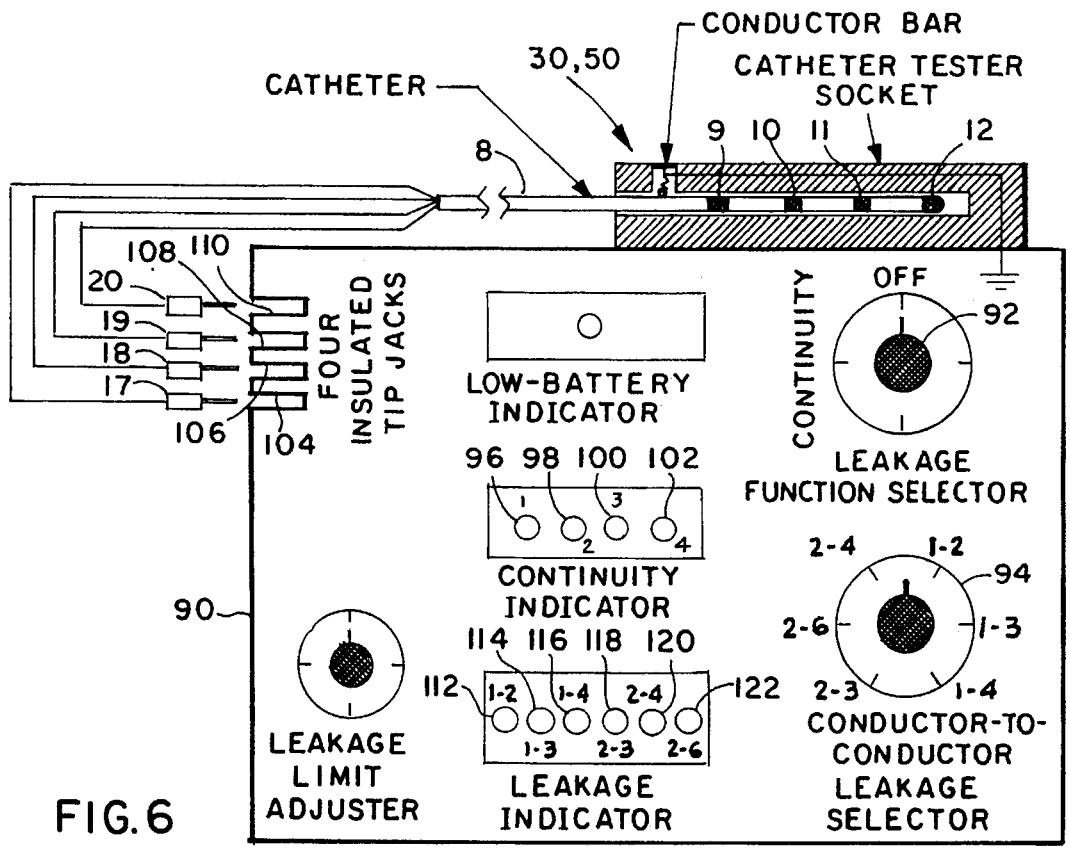
FIG. 6 UNIVERSAL ELECTROPHYSIOLOGY CATHETER TESTER (UECT)
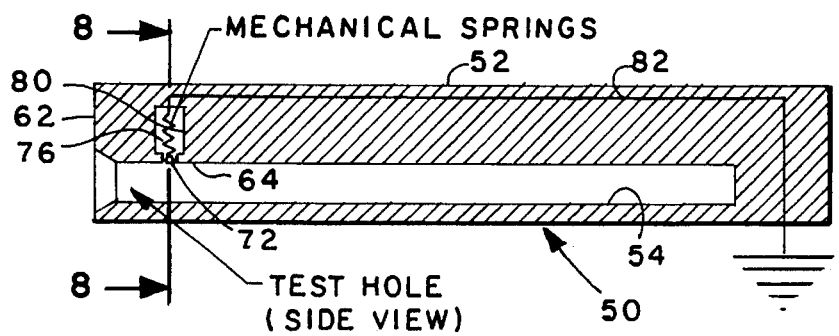
FIG. 7 — LEAKAGE/CONTINUITY SOCKET (LCS), SIDE VIEW
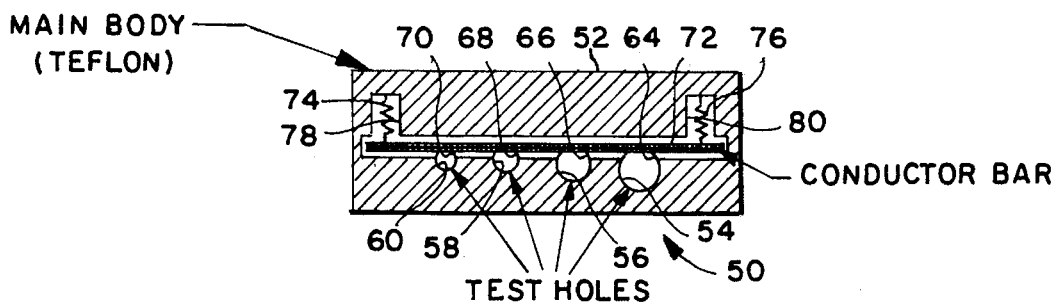
FIG. 8 — LEAKAGE/CONTINUITY SOCKET (LCS), FRONT VIEW

METHOD AND DEVICE FOR TESTING ELECTROPHYSIOLOGY CATHETER

BACKGROUND OF THE INVENTION

The present invention relates to test instruments employed for in situ testing of electrophysiology catheters employed for in vivo studying of the electrical activities of the heart. Typically, catheters of this type contain plural surface electrodes which are of sufficient conductivity that, when inserted into the heart through a vein, the electrical activities of the heart may be remotely monitored through electrical leads extending from the catheter electrodes through the vein and externally of the subject.

Catheters of this type are frequently inserted in a patient experiencing problems with heart function; and, the recordings of the heart electrical activity, as sensed by the catheter electrodes, have proven to be very helpful to medical practitioners in evaluating abnormalities and malfunction of the heart.

Referring to FIG. 1, a plural electrode catheter denoted by Reference numeral 1 is shown inserted through a vein. The catheter is pushed through the vein until the catheter resides in the patients heart denoted by Reference 3. The plural electrodes of the catheter 1 are connected to individual electrical leads denoted by Reference numerals 4, 5, 6, and 7 which may be connected to a device for monitoring the changes in electrical properties of the heart as sensed by the electrodes.

Referring to FIG. 2, a .typical known heart catheter or probe is illustrated as having generally cylindrical electrically non-conductive body denoted by Reference numeral 8 which has disposed therealong at spaced longitudinal stations a plurality of annular electrodes denoted by Reference 9, 10, 11, 12 with the electrode denoted by Reference 12 being disposed at the end of the catheter body 8.

Each of the electrodes 9, 10, 11, 12 has an electrical conductor attached thereto and embedded in the body 8 and extending outwardly from the end thereof remote from the electrode 12 which conductors are denoted respectively by Reference 13, 14, 15, 16 in FIG. 2. It will be understood that the portions of the conductors extending externally of the body 8 are covered with electrically insulating material; and, the remote ends of the conductors each have attached thereto an electrical connector such as a plug jack as denoted by respectively Reference numerals 17, 18, 19, 20. The plug jacks 17, 18, 19, 20 are adapted to be plugged into corresponding sockets provided in an electrical test instrument which is selectively operable by the user to check for continuity and resistance for each of the electrode circuits.

Heretofore, prudent medical practitioners have desired to test a catheter for its electrical integrity. Thus it has been necessary to provide the electrical testing apparatus for this purpose. Known techniques for testing cardiac catheters have utilized a conventional ohm meter for checking continuity individually of each electrode which has required switching of test circuits to evaluate each catheter electrode serially. This procedure has proven to be somewhat complicated and time consuming.

The situation is further complicated by the variety of catheters commercially available to medical practitioners and of the variations in electrode size, spacing and characteristics. Thus, it has long been desired to provide a simple reliable and easy to use way or means of quickly performing the electrical tests on a heart catheter necessary to demonstrate its proper functioning. It has further been desired to provide such a way or means of rapidly testing a cardiac catheter in a way which is not complex and prohibitively costly for manufacture of the test equipment.

SUMMARY OF THE INVENTION

It is an object of the present invention to provide a test apparatus for rapidly and conveniently testing a plural surface electrode cardiac catheter for continuity and leakage in a manner which enables the test equipment to be utilized.

It is a further object of the invention to provide a test apparatus for checking continuity and leakage of a plural surface electrode heart catheter by inserting the catheter in a socket and performing a continuity test on each electrode as it enters the socket.

It is an object of the present invention to provide a test apparatus for performing a leakage test on a plural electrode heart catheter by insertion of the catheter in a socket to a depth where all electrodes are in the socket such that a leakage test is performed across all of the electrodes en masse.

It is an object of the present invention to provide a testing apparatus for a plural surface electrode cardiac catheter by inserting the catheter in a test socket and checking each electrode as it enters the socket for continuity and when all electrodes have entered the socket checking the entire catheter for electrical leakage.

The present invention employs a block or receptacle having a blind bore therein which is sized to receive a cardiac catheter therein; and, the bore has provided therein an electrode adjacent the entrance to the bore which is connected electrically to ground. As each surface electrode enters the bore, the surface electrode makes contact with the grounded electrode in the bore. A voltage applied to the leads for each electrode with a continuity indicator or ohm meter in series therewith indicates the conductivity or lack thereof of each electrode as it enters the bore and contacts the stationary grounded electrode.

In an alternate embodiment, a plurality of test sockets or bores are provided in generally spaced parallel arrangement in the testing apparatus with each of the test sockets or bores sized to receive therein one of the various different sizes of commercially available cardiac catheters. The grounded electrode adjacent the entrance of each of the test sockets or bores comprises a bar extending transversely across a notch or port in each of the bores so that a common grounded electrode may service each of the test sockets.

The present invention employs a potentiometer or variable power supply to apply a voltage across the end electrodes of the plurality of surface electrodes on the catheter while the catheter is in the test socket to determine if there is any high voltage breakdown or leakage across the catheter electrodes. This is accomplished by inserting the catheter in the socket such that all electrodes have passed the stationary grounded electrode and the applied voltage is only to the

BRIEF DESCRIPTION OF THE DRAWINGS

FIG. 2 is a cross-section of a typical plural surface electrode cardiac catheter;

FIG. 3 is a cross-section of the test apparatus of the present invention;

FIG. 6 is a pictorial of the test apparatus of the present invention mounted on the cabinet containing the electrical circuitry for performing the continuity and leakage tests; and, FIG. 7 is a cross-section of an alternate embodiment of the present invention; and, FIG. 8 is a section view taken along section indicating lines 8—8 of FIG. 7.

DETAILED DESCRIPTION

Figure 1:
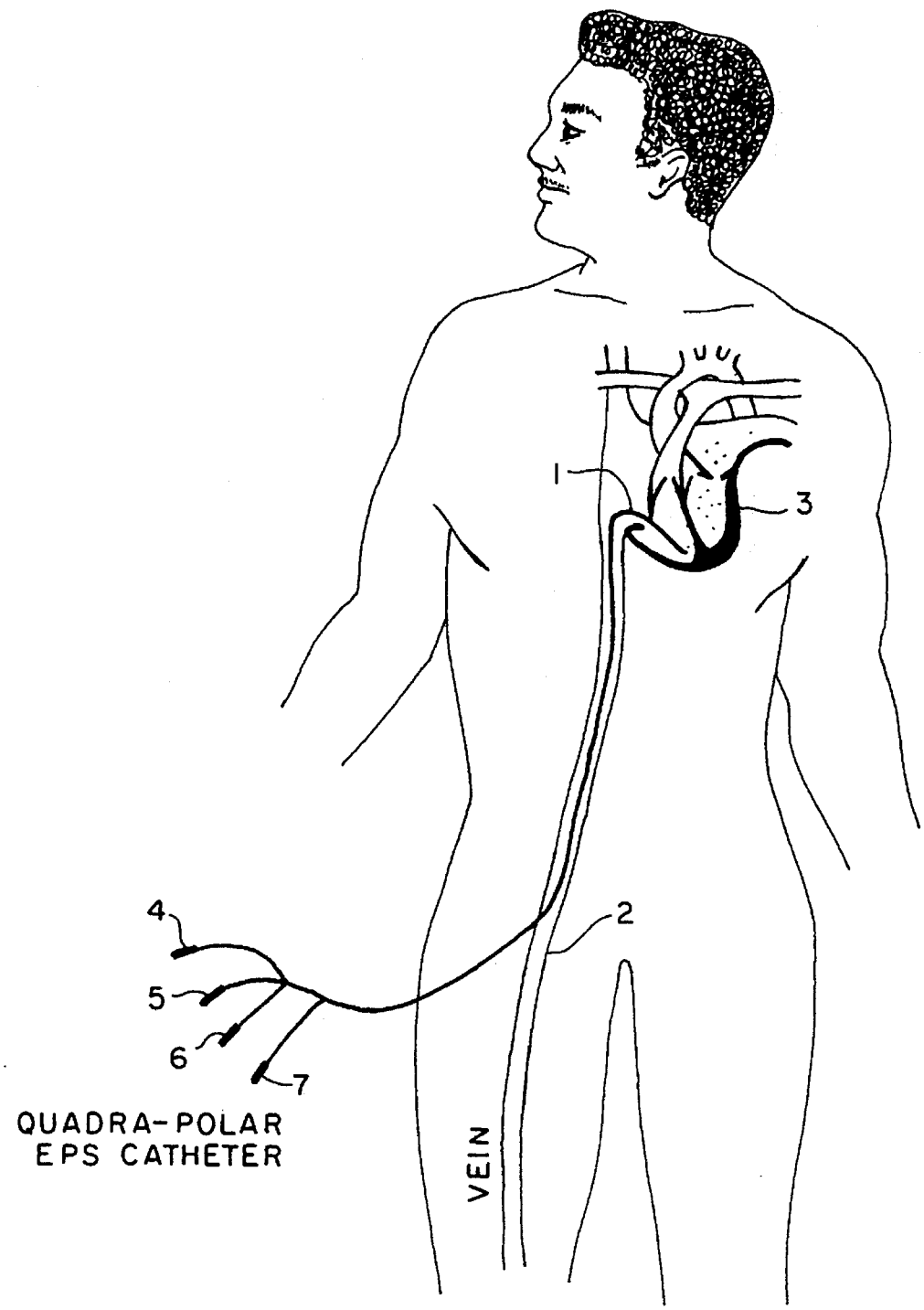
FIG. 1 is a pictorial of a cardiac catheter inserted in a patient in vivo for he, an monitoring.

Referring to FIG. 2, a typical cardiac catheter 8 is illustrated wherein the distance between the electrodes 9 and 10 is denoted by $L_1$ and which is typically uniform for the remaining electrodes spacings for electrodes 11, 12. The width of each of the electrodes 9, 10, 11 is denoted by $L_2$ and the overall length of the electrode array is denoted by $L_3$, with the diameter of the electrode body denoted by the reference character D. The values of the parameters D, $L_1$, $L_2$ and $L_3$ for commercially available cardiac catheters varies widely but may be determined for the more widely available commercially produced catheters from various manufacturers specifications and publications to a degree of specificity that it is possible to provide a test apparatus configured to receive each of the commercially available catheters as will hereinafter be described.

Referring to FIG. 3, the typical cardiac catheter is shown as inserted into the bore 34 of the embodiment 30 of the invention to adept sufficient for the electrode 10 to be contacted by electrical contact ball 40 disposed in a transverse bore 38 formed in cover 36 adjoined to base 32. Ball 40 is biased downwardly by the lower end of spring 42 disposed in bore 38, with the upper end of the spring registered against the blind end of bore 38. The upper end of spring 42 is connected to electrical lead 44 which extends through cover 36 and base 32 to earth ground.

Figure 4:
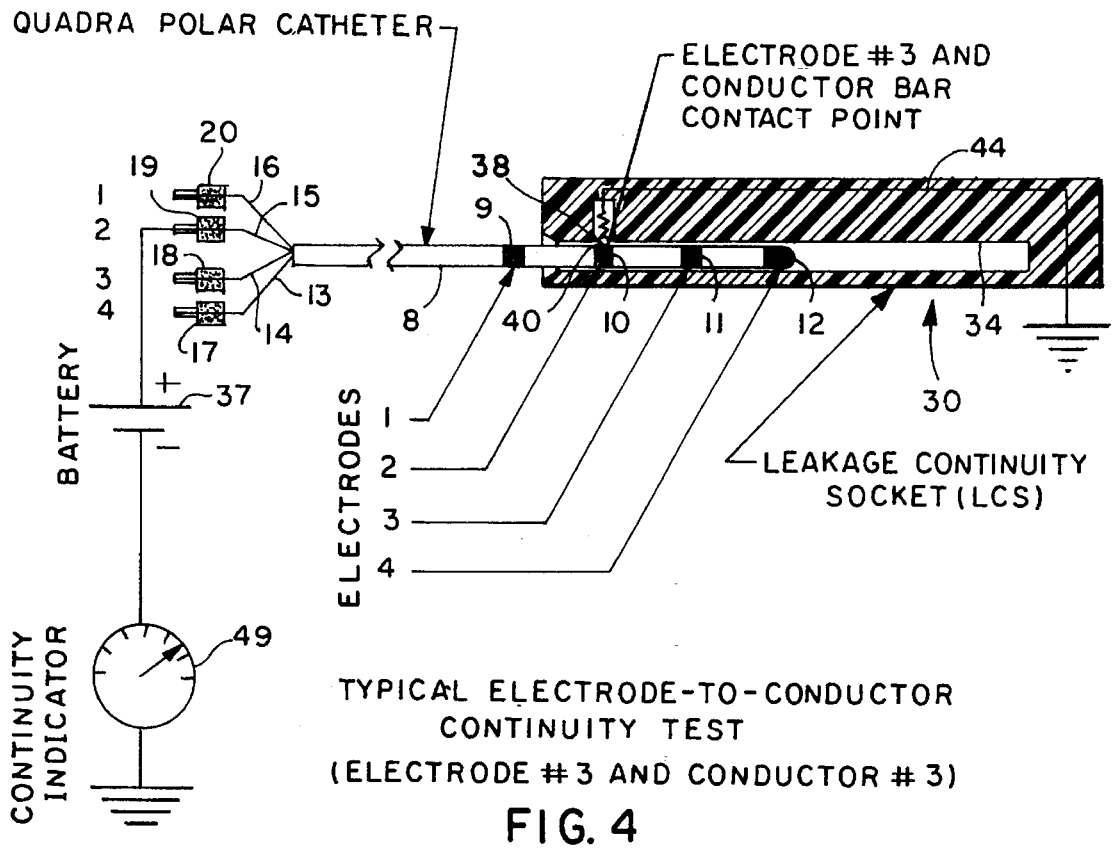
FIG. 4 is an electrical schematic of the apparatus of the present invention with a catheter inserted for performing continuity tests on one of the electrodes.

Referring to FIG. 4 the arrangement of FIG. 3 is shown with conductor 15 via connector 19 connected to a positive terminal of a battery 37 with the negative terminal of battery 37 connected to earth ground through a continuity indicator or meter 49.

In operation, the battery applies a voltage to electrode 10 through conductor 15 and connector 19 indicates a current flow through the continuity indicator 49 only if electrode 10 is functioning properly and an open circuit condition is not present. Similarly, by selectively positioning catheter 8 such that any one of electrodes 11, 12, and 9 is in position to contact ball 40, the function of catheter by the electrodes 11, 12, and 9 may be individually checked by respectively conductors 14, 13 and 16 respectively through connections 18, 17 and 20 to the battery positive terminal.

Figure 5:
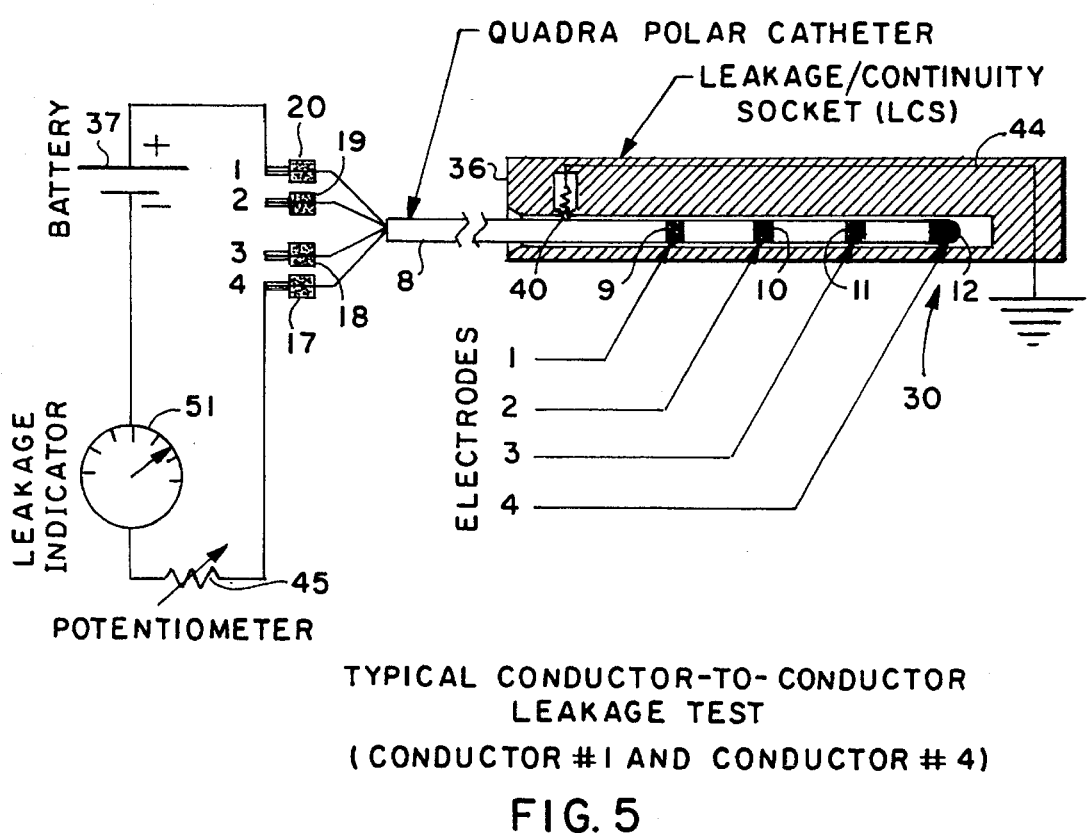
FIG. 5 is an electric schematic of the test apparatus of the present invention with a cardiac catheter inserted fully therein for an overall leakage test.

Referring to FIG. 5, the catheter 8 is shown inserted in bore 34 an amount to position all electrodes 9, 10, 11, 12 past ball 40 with end electrode 9 connected via connector 20 to the positive terminal of battery 37; and, the opposite end electrode 12 of catheter 8 is connected via connector 17 and a trim potentiometer, connected in series with a leakage indicator or meter 51, to the negative terminal of battery 37. The circuit hook-up of FIG. 5 thus permits an overall leakage check of catheter 8.

Referring to FIGS. 7 and 8, another embodiment of the invention indicated generally at 50 is illustrated as having a body 52 with a plurality of bores of different diameter formed therein as blind bores in generally spaced parallel arrangement as denoted by Reference 54, 56, 58, 60. It being understood that only one of the bores, denoted by Reference 54, is shown in the section view of FIG. 7. The bores 54, 56, 58, 60 have different diameters, each of which is chosen to accommodate one of the commercially available cardiac catheters.

Each of the bores 54, 56, 58, 60 has formed therein at a common longitudinal station therealong a slot or port denoted respectively by Reference (34, 66, 68, 70 and which have received therein a common conductor bar 72 which extends across all of the bores. Conductor bar 72 is contacted at its ends by electrically conductive springs denoted respectively by Reference 76, 74, which are received in cavities 78, 80 formed adjacent the ends of the bar 72 in the block 52. Each of the springs 74, 76 has connected thereto a grounding lead one of which is shown in FIG. 7 and denoted by Reference 82.

Thus, the embodiment of FIG. 50 may be employed for quickly performing continuity and leakage tests on any of the commercially available catheters by merely inserting the catheter in one of the holes or bores 54, 56, 58, 60 and making contact with the conductive bar 72 for performing the tests in the same manner as described with respect to the embodiment of FIGS. 4 and 5.

Referring to FIG. 6, the apparatus of the embodiments 30, 50 is shown mounted on a cabinet 90 which houses the electrical circuitry described in FIGS. 4 and 5 and which has selector knobs denoted respectively 92, 94 for dialing the selected test function, i.e. continuity or leakage, and further has indicator lights 96, 98, 100, 102 for indicating continuity of the respective electrode on the catheter. Sockets denoted by Reference 104, 106, 108, 100 are provided for receiving respectively each of the plug jacks 17, 18, 19, 20. Indicator lights denoted by Reference 112, 114, 116, 118, 120, 122 are provided to indicate the results of the leakage tests. It will be understood that the leakage test may be performed sequentially on the catheter conductors 9, 10, 11, 12 as the catheter is progressively fully inserted into the test bore. During the leakage test, the test bore provides only mechanical nonconductive support for the catheter. Voltage may be applied across any selected two conductors via the catheter leads by contacting one electrode with ball 40 and applying voltage to electrical lead for another, in addition to connecting the electrodes as shown in FIG. 5 for overall leakage check. If any electrical leakage is present between the selected conductors, a leak current is detected by a leakage detector. User rotation of 94 to the position indicative of the desired pair of surface electrodes applies the test voltage to the appropriate pair of leads 17, 18, 19, 20 for selectively checking for leakage between the desired pair or surface electrodes. When any of the probe surface electrodes 9, 10, 11, 12 is in contact with ball 38 in embodiment 30 or rod 72 in embodiment 50 for continuity testing, the appropriate indicator 96, 98, 100 or 102 will be illuminated if continuity exists.

Thus, the apparatus of the present invention and the method described herein provide for rapid continuity testing of each electrode and leakage testing of the overall catheter. The apparatus and method of the present invention thus enable medical practitioners to determine the electrical integrity of a catheter and its operating condition and that is functioning satisfactorily.

Although the invention has been hereinabove described with respect to the illustrated embodiment, it will be understood that the invention is capable of modification and variation and is limited only by the following claims.

I claim:

1. A new method of testing a heart catheter/probe having a plurality of spaced surface electrical conductors each having an electrical lead attached thereto comprising:

(a) providing a base or block and forming at least one open cavity in the block;

(b) forming an access port in said block and communicating said port with said cavity and disposing an electrode in said port and extending same into said cavity;

(c) inserting said probe in said cavity and selectively positioning said probe for individually contacting selected ones of said conductors with said electrode; and, (d) applying an electrical potential to the electrical lead associated with said selected one conductor and detecting if current flows through said electrode thereby testing each of said conductors for continuity.

2. The method defined in claim 1, wherein said step of disposing an electrode includes resiliently biassing a contact bar or ball into said port.

3. The method defined in claim 1, wherein said step of forming a cavity includes forming a plurality of generally spaced parallel cavities of different sizes.

4. The method defined in claim 1, wherein (a) said step of forming a cavity includes forming a plurality of generally spaced parallel cavities of different sizes;

(b) said step of forming an access port includes aligning the ports for each of said plurality of cavities; and, (c) said step of disposing an electrode includes interconnecting said ports for said plurality of cavities with a common electrode member.

5. A method of testing a heart catheter/probe having a plurality of spaced surface conductors with individual electrical leads connected thereto;

(a) providing a base or block and forming an open cavity in the block sized to receive the probe in sliding engagement;

(b) forming an access bore in said block communicating said with said cavity;

(c) disposing an electrode in said bore and extending same into said cavity;

(d) inserting said probe in said cavity and selectively positioning said probe and contacting individually selected ones of said conductors with said electrode; and, (e) applying a voltage to another of said conductors through one of said leads and detecting if electrical current flows through said electrode.

6. A tester for electrophysiology catheter/probe of the type having plural spaced surface electrodes each with an individual electrical lead attached comprising:

(a) base or support means having at least one cavity therein sized for slidably receiving said catheter/probe in closely fitting arrangement;

(b) a test electrode disposed at a predetermined location in said at least one cavity and electrical test lead means connected to the test electrode for external connection thereto;

(c) indicator means connected in series with one of said individual electrical leads and a source of electrical potential, wherein, upon user positioning of said probe in said at least one cavity for said test electrode to contact the surface electrode associated with said individual lead, and upon connecting said test lead means in circuit with said power source, current flows through said indicator means if said surface electrode of said probe is functional.

7. The tester defined in claim 6, wherein said base or support means includes a plurality of said bores of different sizes disposed in spaced generally parallel arrangement.

8. The tester defined in claim 6, wherein (a) said base or support means includes a plurality of said bores of different sizes disposed in spaced generally parallel arrangement; and, (b) said electrode includes a common member having different portions thereof extending into each of said plurality of bores.

* * * * *